United States Patent [19]
Olson

[11] Patent Number: 5,380,780
[45] Date of Patent: Jan. 10, 1995

[54] ABSORBABLE COATING AND BLEND

[75] Inventor: James R. Olson, Norwich, Conn.

[73] Assignee: Deknatel Technology Corporation, Inc., Fall River, Mass.

[21] Appl. No.: 944,861

[22] Filed: Sep. 14, 1992

Related U.S. Application Data

[63] Continuation of Ser. No. 291,486, Dec. 29, 1988, abandoned.

[51] Int. Cl.$^6$ .................. C08J 5/10; A61L 17/00
[52] U.S. Cl. .................. 524/311; 524/306; 524/312; 524/313; 524/317; 524/322; 606/230; 606/231
[58] Field of Search ............... 525/415, 411; 524/379, 524/380, 313, 311, 322, 312, 306, 317; 523/105; 606/230, 231; 428/394, 395, 375, 364

[56] References Cited

U.S. PATENT DOCUMENTS

| | | | |
|---|---|---|---|
| 2,576,576 | 11/1951 | Cresswell | 606/230 |
| 3,297,033 | 1/1967 | Schmitt et al. | 606/230 |
| 3,636,956 | 1/1972 | Schneider | 128/335.5 |
| 3,797,489 | 3/1974 | Schneider | 128/334 |
| 3,896,814 | 7/1975 | Vivien et al. | 606/229 |
| 3,942,532 | 3/1976 | Hunter et al. | 606/230 |
| 4,027,676 | 6/1977 | Mattei | 428/378 |
| 4,095,600 | 6/1978 | Casey et al. | 606/230 |
| 4,201,216 | 5/1980 | Mattei | 606/230 |
| 4,624,256 | 11/1986 | Meissier et al. | 606/230 |
| 4,700,704 | 10/1987 | Jamiokowski et al. | 128/335.5 |
| 4,711,241 | 12/1987 | Lehmann | 606/230 |
| 4,791,929 | 12/1988 | Jarrett et al. | 606/230 |
| 4,844,067 | 7/1989 | Ikada | 606/230 |
| 5,312,437 | 5/1994 | Hermes et al. | 606/230 |
| 5,314,989 | 5/1994 | Kennedy et al. | 606/230 |

OTHER PUBLICATIONS

Pitt, C. G. et al.; Aliphatic Polyesters I. The Degradation of Poly ($\epsilon$-Caprolactone) In Vivo; Journal App. Polymer Science, vol. 26, pp. 3779–3787 (1981) (1988).

Primary Examiner—Patrick J. Ryan
Assistant Examiner—J. M. Gray
Attorney, Agent, or Firm—Pennie & Edmonds

[57] ABSTRACT

Absorbable coating and absorbable blend of polycaprolactone and crystallization modifier especially suitable for use in the coating of surgical sutures and in the controlled release of chemical or pharmaceutical agents.

7 Claims, No Drawings

ABSORBABLE COATING AND BLEND

This is a continuation, of application Ser. No. 07/291,486, filed Dec. 29, 1988, now abandoned.

BACKGROUND OF THE INVENTION

The present invention pertains generally to absorbable coatings and absorbable blends for surgical sutures and drug delivery systems. More particularly, the invention relates to absorbable compositions which might include a homopolymer of $\epsilon$-caprolactone and a crystallization modifier or a copolymer of $\epsilon$-caprolactone, an absorbable monomer, and a crystallization modifier.

During the past thirty years, the use of synthetic absorbable polymers in medical devices and drug delivery systems has made a dramatic rise. Foremost in the area of absorbable medical devices has been the usage of absorbable polyesters that are usually aliphatic and linear. For example, in the area of wound closure, there has been extensive application of the homopolymer poly(glycolic acid), see for example U.S. Pat. No. 3,297,033, and copolymers of glycolic acid with a variety of other monomers which produce likewise absorbable polymers, see for example U.S. Pat. No. 3,839,297.

Dependent upon the specific application, there is a preferred time window where the synthetic polymer has completely absorbed, that is, has lost all of its mass to the surrounding tissue. In the case of absorbable sutures in sewn tissue after surgery, that window is usually within one year, although even shorter times are more preferable (U.S. Pat. Nos. 4,027,676 and 4,201,216). For other applications this time window could be either shorter or longer. Thus, for a given application there is a need to use absorbable polymers that degrade within the time limits of that application.

There is some leeway in the selection of synthetic absorbable polyesters for a given application since the rates of the hydrolysis of this class of polymers do vary over a wide range. Differences in the rates of hydrolysis of absorbable synthetic polyesters can be attributed to the intrinsic hydrolytic stability of their specific ester linkages and to the physical properties of their respective polymers. For instance, the hydrolytic stability of the ester linkage is strongly influenced by both electronic and steric factors. An example of an electronic effect is the increased reactivity of ester linkages which have a hydroxy substitution $\alpha$ to the ester linkage, as in the case of esters of glycolic acid. Physical properties which are important to the hydrolytic behavior and subsequent mass loss in synthetic absorbable polyesters include the glass transition temperature and the degree of crystallization in the polymer. In semi-crystalline polymers like poly(glycolic acid) and polycaprolactone, it has been hypothesized that hydrolysis takes place initially in the amorphous areas of the polymer, where migration or absorption of the water molecule is facile compared to the crystalline areas. Thus it appears that the water molecule prior to reaction at an ester linkage of a synthetic absorbable polyester must first have access or absorption into the polymer. Crystalline areas of the polymer have been hypothesized to impede the access or penetration of water molecules. Therefore, to the extent that this takes place, the overall hydrolytic breakdown of the absorbable polyester is retarded. In the case of polycaprolactone, the hydrolytic degradation rate and subsequent mass loss is also dependent upon particle size, wherein small particles degrade and lose mass much more rapidly than a polymer cast in film form.

One application of synthetic polyesters is in the coating of surgical sutures. The coating on a surgical suture is very important in providing good knotting performance, as explained in U.S. Pat. No. 3,390,681, where the snug down performance of a braided nonabsorbable poly(ethylene terephthalate) suture under both dry and wet conditions was improved by deposition of small particles of non-absorbable polytetrafluoroethylene. Tie-down performance of braided polyethylene terephthalate has also been disclosed to be improved through its coating with linear polyesters (U.S. Pat. No. 3,942,532) such as polycaprolactone. It was further disclosed in U.S. No. 3,942,532 that polycaprolactone of molecular weight in the range of 1,000 to 15,000 may also be used to coat synthetic absorbable sutures. However, polycaprolactone is known to be a slowly absorbable synthetic polyester, that may not meet the absorption time window, as it is known in the art, for an absorbable suture. Indeed, in subsequent U.S. Pat. Nos. 4,027,676 and 4,201,216 it is pointed out that the disclosure of linear polyesters for use with absorbable sutures in U.S. Pat. No. 3,942,532 did not consider that the sutures would not be totally absorbable. On the other hand, high molecular weight polycaprolactone has been disclosed in U.S. Pat. No. 4,624,256 to provide improved tie down performance and knot security to braided multifilament poly(glycolic acid) sutures under both dry and wet conditions. Thus, the art clearly demonstrates the usefulness of polycaprolactone as a coating for sutures in terms of tie-down performance and knot security. However, the use of an absorbable polymer must be matched with its allowable time window for complete absorption for a given application. Thus there is a need to be able to regulate the in vivo absorption profile of absorbable polymers to meet the criteria of specific applications.

An object of the invention is to increase the in vivo absorption rate of polycaprolactone by blending it with crystallization modifiers that reduce the amount of crystallinity in the polymer. Thus its rate of hydrolysis and subsequent mass loss can be regulated in order to meet the needs of a specific application. A further object of the invention is to provide an absorbable coating for absorbable sutures which meets the time window of complete absorption within one year of surgery and provides good tie-down performance under both dry and wet conditions. An additional object of the invention is to provide a controlled absorbable matrix for the controlled release of chemical for pharmaceutical agents.

SUMMARY OF THE INVENTION

The present invention is directed toward an absorbable coating for a surgical suture comprising a homopolymer of $\epsilon$-caprolactone and a crystallization modifier. The suture is preferably an absorbable suture. The crystallization modifier might be either a crystalline fatty acid or a crystalline ester of a fatty acid. Preferably, the crystallization modifier is a crystalline ester of a fatty acid. Particularly suitable crystallization modifiers are crystalline esters of fatty acids which are saturated $C_{12}$–$C_{18}$ fatty acid esters of polyhydric alcohols. Preferably, the polyhydric alcohols might be glycerol, ethylene glycol or propylene glycol.

The coating composition includes a range from about 95 to about 5% by weight of the homopolymer of $\epsilon$- caprolactone and a range of from about 5 to about 95% by weight of the crystallization modifier. In one composition, the homopolymer of ε-caprolactone ranges from about 70 to about 30% by weight and the crystallization modifier ranges in weight from about 30 to about 70%. In a specific composition, the homopolymer of ε-caprolactone and the crystallization modifier are each about 50% by weight. The homopolymer of ε-caproalctone has a molecular weight of at least about 1,000 and a molecular weight range of preferably from about 15,000 to about 40,000.

Also included within the scope of the invention is an absorbable blend comprising a homopolymer of ε-caprolactone and a crystallization modifier. The present invention further includes an absorbable surgical suture comprising at least one filament of poly(glycolic acid) coated with an absorbable coating which comprises a homopolymer of ε-caprolactone and a crystallization modifier. The suture further comprises a copolymer having at least about 85% glycolic acid units.

The invention further embodies an absorbable controlled release matrix comprising a blend of a homopolymer of ε-caprolactone and a crystallization modifier. The matrix further includes either a chemical or a pharmaceutical agent. The matrix crystallization modifier might either be a crystalline fatty acid or a crystalline ester of a fatty acid, preferably the latter. Suitable crystallization modifiers are crystalline esters of fatty acids which are saturated $C_{12}$–$C_{18}$ fatty acid esters of polyhydric alcohols, preferably such as glycerol, ethylene glycol or propylene glycol. The matrix homopolymer of ε-caprolactone ranges in weight from about 95 to about 5% by weight of the blend and the crystallization modifier ranges in weight from about 5 to about 95% by weight of the blend.

In a further embodiment, the invention includes an absorbable blend comprising a copolymer of at least about 80% by weight of ε-caprolactone and corresponding remainder weight of another absorbable monomer, and a crystallization modifier. The blend further includes either a chemical or pharmaceutical agent.

The invention further embodies a method for effecting the rate of absorption of polycaprolactone comprising the step of blending a homopolymer of ε-caprolactone and a crystallization modifier. The absorption rate increases as the blend ratio of the crystallization modifier to the homopolymer of ε-caprolactone increases.

DETAILED DESCRIPTION OF THE PREFERRED EMBODIMENTS

The in vivo absorption rate of polycaprolactone can be increased by blending the polymer with crystalline fatty acid esters of polyhydric alcohols, which function as crystallization modifiers. Furthermore, the rate of this absorption can be regulated by control of the amount of added crystalline modifier. The blending of these fatty acid esters with the polycaprolactone do not however adversely effect its excellent coating properties. Thus the poly-caprolactone-fatty acid ester blends of the present invention are an excellent absorbable coating for absorbable sutures such as those of braided poly(glycolic acid). Moreover, these blends can be used in the controlled release of chemical or pharmaceutical agents.

The rate of hydrolysis and subsequent mass loss in the hydrolytic degradation of polycaprolactone has been increased through the blending of the polycaprolactone with a crystallization modifier. In essence, the crystallization modifiers have been found to reduce the amount of crystallization in the polycaprolactone and to also retard the film forming ability of polycaprolactone that has been cast from solution in a volatile solvent. Remarkably, the blending of the polycaprolactone with the crystallization modifiers of the present invention does not adversely affect the desired properties of the polycaprolactone. The crystallization modifiers of the present invention are themselves crystalline in nature and readily form homogeneous solid blends with polycaprolactone either by casting from a solution of each or by preparation from a melt. This suggests an intimate interaction and compatibility between the polycaprolactone and the non-polymer crystallization modifiers.

In this invention, both homopolymers and copolymers of ε-caprolactone are suitable for blending with a crystallization modifier. Homopolymers of ε-caprolactone should have a minimum molecular weight of at least about 1000. However, there is no maximum limit that is applicable to the homopolymer. A variety of molecular weights in polycaprolactones is commercially available from Union Carbide Corporation under the Tone brand name. For example, lower molecular weight polycaprolactones are available as Tone Polyols, while higher molecular weight polycaprolactones are available as Tone PCL-300 and Tone PCL-700, which have weight average molecular weights of 15,000 and 40,000, respectively, as reported by the manufacturer. Copolymers of ε-caprolactone are those synthesized from at least about 80% by weight of the ε-caprolactone monomer and the corresponding remainder of another absorbable monomer. The copolymers could be either random or block copolymers. Absorbable monomers consistent with these copolymers include glycolic acid, lactic acid, and other aliphatic hydroxycarboxylic acids which are usually polymerized from their corresponding lactones, that is, glycolide, lactide, etc. Such copolymers, which contain a high percentage by weight of polycaprolactone segments, can have their in vivo absorption rates increased by their blending with crystallization modifiers.

In this invention, crystallization modifiers have been found which affect the crystallinity of polycaprolactone and its film forming ability. The preferred crystallization modifiers have been found to be saturated $C_{12}$–$C_{18}$ fatty acid esters of polyhydric alcohols. Polyhydric alcohols useful in this invention are, for example, glycerol, ethylene glycol and propylene glycol. Commercial sources of these materials, which are often a mixture of compounds like glycerol monostearate (also contains glycerol palminate for instance), are suitable in this invention. Such esters are crystalline in nature, that is, show characteristic X-ray powder diffraction patterns of crystalline matter. It is believed that this inherent crystallinity of these fatty acid esters allows for a crystalline interaction with the "semi-crystalline" polycaprolactone, which produces a lower net crystallinity in the blend. Furthermore, that this disruption in crystallinity in the net blend and in the constituent polycaprolactone is responsible for the disruption in film forming ability in the polycaprolactone. Thus, two factors of critical importance in the rate of hydrolytic degradation and subsequent mass loss of polycaprolactone can be controlled by the addition of the crystallization modifiers of this invention. Another important characteristic of these crystallization modifiers is that they are water insoluble, but enzymatically degradable. Therefore, the crystallization modifiers will not be rapidly leached out of their crystalline interaction with the polycaprolactone and can prevent the re-crystallization of the polycaprolactone as it is subject to hydrolytic degradation in its molecular weight.

X-ray powder diffraction spectra have been taken on polycaprolactone-700 (PCL-700) (Union Carbide), glycerol monostearate (GMS) pure (Stepan Chemical Co.), physical mixtures of the two components, and blends of the two components. The physical mixture of the two components was prepared by mixing equal amounts of powdered PCL-700 and GMS together at room temperature. The blends were prepared for the diffraction experiments by first dissolving the two solutes in a methylene chloride/methanol solvent to give about a 10% by weight solution. Next, the solvent was evaporated to leave the solid blend, which was carefully ground with a mortar and pestle to produce uniform powder. Diffraction patterns were recorded in the range of $2\theta$ values of 10° to 30° with a powder diffractometer using copper $K\alpha$ radiation. Maximum diffraction intensities were observed in this range for the polycaprolactone, the glycerol monostearate, the physical mixture, and the respective blends. The total area underneath each diffraction pattern was quantified, then scaled to a relative area based upon the physical mixture having an area value of 100. The relative area for each sample is a measure of its total crystallinity. A comparison of the relative areas under the diffraction patterns in this range is given in Table 1.

TABLE I

| COMPOSITION | RELATIVE AREA | % DECREASE IN TOTAL CRYSTALLINITY |
|---|---|---|
| physical mixture 50% PCL + 50% GMS | 100 | — |
| blend 50% PCL + 50% GMS | 65 | 35% |
| blend 33% PCL + 67% GMS | 56 | 44% |
| blend 20% PCL + 80% GMS | 45 | 55% |

Comparison of the diffraction pattern of a 1 to 1 physical mixture of polycaprolactone(PCL) with glycerol monostearate(GMS) to the diffraction pattern of the 1 to 1 blend of the two components, which was prepared as described above, shows a 35% decrease in crystallinity in the blend. Larger decreases in crystallinity occur as the proportion of the glycerol monostearate is increased. Furthermore, it is evident that the crystallinity is decreased in both components. Thus, an intimate interaction between the two components is suggested.

A qualitative assessment of the relative film forming ability of polycaprolactone versus the blends of this invention was carried out by decantation of the respective 10% by weight solutions onto a flat surface and allowing the solvent to evaporate. In this experiment mono-di-glycerides (MDG) (Stepan Chemical Co.) was used as the crystallization modifier for polycaprolactone-700 (Union Carbide). These results are summarized in Table II and show a dramatic decrease in film forming ability as the proportion of the crystallization modifier is increased.

TABLE II

| COMPOSITION | FILM DESCRIPTION |
|---|---|
| 100% PCL | strong, tough, clear |
| 90% PCL + 10% MDG | very weak film, opaque |
| 70% PCL + 30% MDG | forms white layer, weak cohesion |
| 50% PCL + 50% MDG | forms white solid, weak cohesion |
| 30% PCL + 70% MDG | forms white particulate solid |
| 10% PCL + 90% MDG | forms white particulate solid |

The film forming tendencies of the blends of this invention were further investigated by following coated poly(glycolic) (PGA) suture integrity under in vitro conditions. For example, size 0 braided poly(glycolic acid) sutures uncoated, coated with 100% polycaprolactone-700 (Union Carbide), and coated with a 1 to 1 blend of polycaprolactone-700 (Union Carbide) and glyceryl monostearate pure (Stepan Chemical Co.) were each immersed in buffer solution at a pH of 7.0 in test tubes and placed in a constant temperature bath at 50° C. The coated sutures had coating weight pick-ups of 7 and 5% for the PCL-700 and the 1 to 1 blend, respectively. Visual inspection of the sutures was recorded over time. By Day-48 both the uncoated PGA suture and the suture coated with a blend of PCL/GMS had degraded to a lint-like residue. However, the PCL coated suture was only broken into small rigid segments. This appearance of the PCL coated suture was unchanged at Day-78 and suggested that the suture was encapsulated by a strong, tough film of the polycaprolactone. On the other hand, both the uncoated suture and the suture coated with a 1 to 1 blend of PCL/GMS exhibited a similar degree of degradation in the same time frame of 48 days.

Although the primary object of this invention is to influence and regulate the rate of hydrolysis and mass loss in polycaprolactone, this objective should not be achieved at the expense of its application benefits. In the case of its application as an absorbable suture coating it has been found that the coating effectiveness of the various blends is actually increased over that of 100% PCL. Thus it appears that the blending of polycaprolactone with the crystallization modifiers of this invention enhances the softness and pliability of the suture as compared to a suture coated with only polycaprolactone.

The blends of polycaprolactone and crystallization modifiers of the present invention also have application in the controlled release of chemical and pharmaceutical agents. Indeed, the proportion of crystallization modifier to polycaprolactone can be used to regulate the rate of release of chemical or pharmaceutical agents. Moreover, these blends have improved rates of mass loss when compared to matrices of 100% PCL. The blending of polycaprolactone with a crystallization modifier like glycerol monostearate thus produces an absorbable matrix with many beneficial attributes. Besides the benefit of regulated release and mass loss, blends of this invention are expected to in general release agents faster than that of 100% polycaprolactone, yet much slower than 100% of a crystallization modifier like glycerol monostearate.

The following illustrate, by way of example, use of an absorbable blend for an absorbable suture (Example 1) and an absorbable controlled release matrix (Example 2).

Example 1

A coating solution comprised of the following by weight percent, 5.5% polycaprolactone-700 (Union Carbide), 5.5% mono-di-glycerides (Stepan Chemical Co.), 9% methanol, and 80% methylene chloride, was used to coat absorbable braided sutures of poly(glycolic acid) in the size range from size 2 to 6/0. A continuous feed of the spooled uncoated suture was passed for a short time at a fixed rate through the coating solution, then allowed to air dry before winding onto a take-up spool. The coated sutures showed a dry weight coating pick-up in the range of about 2 to 5% depending upon size. The coated suture has excellent handling and tie-down properties under both dry and wet conditions for all sizes. Comparison of the implantation of this sterile coated suture versus that of the sterile uncoated suture in rats, has shown that the coating does not effect the in vivo tensile strength of the suture during the critical time period of wound healing. Additionally, over a longer time period, both the coated and uncoated sutures exhibited a similar rate of absorption. Comparison of the implantation of the sterile coated suture of this invention versus sterile poly(glycolic acid) sutures coated with only polycaprolactone 700 in rats, has shown that the coated sutures of this invention show complete absorption before those sutures coated with just polycaprolactone. Furthermore, the coated sutures of this invention show complete absorption of suture and coating, well within a time window of one year.

Example 2

Application of absorbable blends of polycaprolactone and a crystallization modifier as an absorbable controlled release matrix was demonstrated by following the in vitro release of methylene blue (Aldrich Chemical Co.) from thin disks of the absorbable matrix. Methylene blue is a water soluble dye and was used to mimic the release of a water soluble chemical or pharmaceutical agent from the absorbable matrix. Absorbable controlled release matrices containing methylene blue were prepared as follows. Portions of solid polycaprolactone-700 (Union Carbide) and mono-diglycerides (Stepan Chemical Co.) in relative proportions of 7 to 3, 1 to 1, and 3 to 7 were heated to about 90° C. and stirred to give homogeneous melts. Exactly 0.4% by weight of methylene blue was then mixed into each melt. The melts were then poured onto a cool plate to form disks 2 mm thick. Immersion of equal amounts of disks of each composition in buffer solution of pH 7.0 at a temperature of 50° C. showed a staggered rate of blue dye release as a function of disk composition. The rate of dye release increased with increasing amounts of mono-di-glycerides to polycaprolactone. Moreover, the rates of dye release from the absorbable matrices were greater than that of a similarly prepared disk of 100% PCL-700, but lower than that of similarly prepared disks of mono-di-glycerides.

The present invention has been described herein with specific reference to the preferred embodiments thereof. However, those skilled in the art will understand that changes may be made in the form of the invention covered by the claims without departing from the scope and spirit thereof, and that certain features of the invention may sometimes be used to an advantage without corresponding use of the other features.

I claim:

1. An absorbable coating comprising a blend of about 95 to about 5% by weight of a homopolymer of -caprolactone and about 5 to about 95% by weight of a crystallization modifier selected from the group consisting of crystalline fatty acids and crystalline esters of fatty acids which are saturated $C_{12}$–$C_{18}$ fatty acid esters of polyhydric alcohols.

2. The coating according to claim 1, wherein said crystallization modifier is crystalline esters or fatty acids which are saturated $C_{12}$–$C_{18}$ fatty acid esters of polyhydric alcohols.

3. The coating according to claim 2 wherein said polyhydric alcohols are selected from the group consisting of glycerol, ethylene glycol and propylene glycol.

4. The coating according to claim 1 wherein said homopolymer of -caprolactone is present in the amount ranging from about 70 to about 30% by weight and said crystallization modifier is present in the amount ranging from about 30 to about 70% by weight.

5. The coating according to claim 1 wherein said homopolymer of ε-caprolactone and said crystallization modifier are each present in the amount of about 50% by weight.

6. The coating according to claim 5 wherein said homopolymer of ε-caprolactone has a molecular weight of at least 1,000.

7. The coating according to claim 6 wherein said homopolymer of ε-caprolactone has a molecular weight ranging from about 15,000 to about 40,000.

* * * * *